United States Patent
Yapici et al.

(10) Patent No.: US 10,824,230 B1
(45) Date of Patent: Nov. 3, 2020

(54) WEARABLE GRAPHENE TEXTILE-BASED ELECTRO-OCULAR MONITORING AND OBJECT INTERACTION SYSTEM

(71) Applicant: Sabanci Universitesi, Istanbul (TR)

(72) Inventors: Murat Kaya Yapici, Istanbul (TR); Ata Jedari Golparvar, Istanbul (TR)

(73) Assignee: Sabanci Universitesi, Istanbul (TR)

( * ) Notice: Subject to any disclaimer, the term of this patent is extended or adjusted under 35 U.S.C. 154(b) by 0 days.

(21) Appl. No.: 16/517,303

(22) Filed: Jul. 19, 2019

(51) Int. Cl.
   *G06F 3/01* (2006.01)
(52) U.S. Cl.
   CPC .................................. *G06F 3/013* (2013.01)
(58) Field of Classification Search
   None
   See application file for complete search history.

(56) References Cited

U.S. PATENT DOCUMENTS

| | | | |
|---|---|---|---|
| 2004/0070729 A1* | 4/2004 | Wiebe | A61B 5/6803 351/209 |
| 2018/0169412 A1* | 6/2018 | Goodall | A61N 1/0541 |
| 2019/0365272 A1* | 12/2019 | Sadeghian-Motahar | A61B 5/0496 |

OTHER PUBLICATIONS

Wu et al., "Controlling a Human-Computer Interface System With a Novel Classification Method that Uses Electrooculography Signals," dated Aug. 2013, pp. 2133-2141, vol. 60, No. 8, IEEE Transactions on Biomedical Engineering.
López et al., "EOG-based system for mouse control," dated Jul. 22, 2014, pp. 1264-1267, Sensors, IEEE.
López et al., "Development of a computer wiring system based on EOG," dated Jun. 26, 2017, pp. 1-20, vol. 17, No. 7, 1505, Sensors.
Barea et al., "System for assisted mobility using eye movements based on electrooculography," dated Dec. 2002, pp. 209-218, IEEE Trans. Neural. Syst. Rehabil. Eng.
Ubeda et al., "Wireless and portable EOG-based interface for assisting disabled people," dated Oct. 2011, pp. 870-873, vol. 16, No. 5, IEEE ASME Trans. Mechatron.
López et al., "Development of and EOG-based system to control a Serious Game." dated Jun. 15, 2018, pp. 481-488, vol. 127, Measurement.
Bulling et al., "Eye movement analysis for activity recognition using electrooculography," dated Apr. 2011, pp. 741-753, vol. 33, No. 4, IEEE Trans. Pattern Anal. Mach. Intell.
Ebrahim et al., "Eye movement detection for assessing driver drowsiness by electrooculography," dated Sep. 24, 2013, pp. 4142-4148, Proc. IEEE Int. Conf. Sys. Man Cyber., Manchester, UK.
Vidal et al., "Wearable eye tracking for mental health monitoring" dated Jun. 8, 2012, pp. 1306-1311, vol. 35, No. 11, Computer Communications.

* cited by examiner

*Primary Examiner* — Christopher J Kohlman
(74) *Attorney, Agent, or Firm* — Brinks Gilson & Lione

(57) ABSTRACT

The system proposes an electrooculogram based human computer interaction/human machine interface (HCI/HMI) system comprising wearable graphene textiles, a signal acquisition system for obtaining biopotentials from the human body, and a processor for the processing of said biopotentials acquired through said signal acquisition system for enabling and facilitating human machine interactions in various settings.

15 Claims, 6 Drawing Sheets

WEARABLE GRAPHENE TEXTILE-BASED ELECTRO-OCULAR MONITORING AND OBJECT INTERACTION SYSTEM

BACKGROUND

Technical Field

This disclosure relates to devices/methods for eye movement-enabled machine interaction with wearable peripherals. The disclosure more specifically concerns forehead electrooculography based human computer interaction (HCI) and human machine interface (HMI) systems, comprising gel-free signal acquisition means such as dry electrode-enabled wearables.

Background

Measurement of human eye movement may be measured with pairs of electrodes. The electrodes may be placed around human eyes so as to detect movement based on measuring cornea-retinal standing potential, which is present between the front and back of the human eye. The signal resulting from such movement detection may be referred to as an electrooculogram.

SUMMARY

Human eye and its movement have a tremendous source of potential for the rise of new applications in human-computer/machine interfaces (HCI/HMI). Recent technical developments and research target facilitation of human eye movement enablement for control of computers, machines and other tools covering a wide array from health to industry. However, economic challenges and long-term performance of some of the earlier designs obligates successful realization of casual, consumer-driven, and wearable products. Therefore, a significant portion of the effort has been placed to fully investigate different methods to take possession of eye movements (EM) in HCI/HMI interfaces.

For instance, coil-based eye tracking systems are invasive and are not meeting the non-clinical application needs. On the other hand, camera-based eye tracking setups fulfill the invasivity issue and display long-term functionality but they are hardly affordable due to their hardware (e.g. camera) and image processing requirements. Additionally, the camera has to be positioned at a location suitable to capture the eye movements, which limits portability of such systems. Alternatively, electrooculography (EOG) is an economical, non-invasive, and reliable method for acquiring biopotential signals around the eyes and addresses the limitations of both coil and camera-based systems. EOG is essentially based on the simple model of the human eye, which is a dipole where the potential between its forward and backward facing spots generate an electric field. These voltage fluctuations can be detected if a pair of electrodes is attached around the eyes, and by feeding the acquired ocular biopotential signal into a proper processing unit, EMs can be tracked.

So far, several electrooculography-based rehabilitation systems were developed as an assistive technology for people with lock-in syndromes in a study by Wu et al. titled "Controlling a Human-Computer Interface System With a Novel Classification Method that Uses Electrooculography Signals" published in IEEE Transactions on Biomedical Engineering (vol. 60, no. 8, pp. 2133-2141, August 2013). A human-computer or human-machine interface is able to emulate a PC mouse in a study by Lopez et al. titled "EOG-based system for mouse control," (SENSORS, 2014 IEEE, Valencia, 2014, pp. 1264-1267). Yet another study by Lopez et al. titled "Development of a computer wiring system based on EOG" (Sensors, vol. 17 no 7, pp. 1505, 2017) run a virtual keyboard. Barea et al. in the publication (IEEE Trans. Neural. Syst. Rehabil. Eng. vol. 10 no. 4 pp 209-218, 2002) "System for assisted mobility using eye movements based on electrooculography" drive a wheelchair. Ubeda et al. in "Wireless and portable EOG-based interface for assisting disabled people" (IEEE ASME Trans. Mechatron, vol. 16, no. 5, pp. 870-873, 2011) have reported driving a wheelchair and controlling robots. Lopez et al. in "Development of and EOG-based system to control a Serious Game" (Measurement, vol. 127, pp. 481-488, 2018) teach improvement of user experience on gaming. Additionally, visual fatigue estimation using EOG was proposed to be used in 2D/3D display auto-adjustment switch systems. Moreover, EOG signals are also used in cognitive studies and neurosciences including human activity recognition by Bulling et al. in "Eye movement analysis for activity recognition using electrooculography." (IEEE Trans. Pattern Anal. Mach. Intell., vol. 33, no. 4, pp. 741-753, 2011); sleep studies and drowsiness detection by Ebrahim et al. in "Eye movement detection for assessing driver drowsiness by electrooculography" (Proc. IEEE Int. Conf. Sys. Man Cyber., Manchester, U K, 2013, pp. 4142-4148), and monitoring and diagnosis of mental and sleep disorders by Vidal et al. in "Wearable eye tracking for mental health monitoring" (Computer Communications, vol. 35, no. 11, pp. 1306-1311, 2012).

Despite the various demonstrators of wearable EOG devices in the literature, their full potential has not been realized due to limitations of the sensing electrode. Typically, what is seen in the art is that, signal acquisition units for electrophysiological responses rely on the direct contact of disposable, pre-gelled, "wet" silver/silver chloride (Ag/AgCl) electrodes fixed on the subject's skin with adhesive backing material. Although standard Ag/AgCl electrodes are low-cost, widely available, and capable of providing accurate signal acquisition capabilities, the need for skin preparation severely limits their usability in wearable electronic applications. For instance, the conductive gel dehydrates in time, causing degradation in the electrode performance, thus, once in a few hours, electrodes must be changed or the gel must be re-applied, which is inefficient and time-consuming and not acceptable for everyday and easy-to use applications.

Moreover, said gel can cause an itching sensation; as well as, red and swollen skin which develops immediately upon removal by mechanical peeling of the electrode. Such irritations and allergic reactions may only last for several hours or may even lead to dermatitis. Due to the above concerns, studies have been proposing the elimination of the gel by developing "dry" electrodes, which are more suitable for continuous, autonomous and unsupervised electrophysiological monitoring, and meet the desired comfort level for integration with wearable devices.

One promising approach that emerged in recent years is based on the use of conductive, smart textiles. Owing to their inherent advantages like smooth texture and the ability to be directly weaved into garments, several methods have been suggested to develop textile electrodes for electrophysiological signal monitoring. The main challenge here is to synthesize conductive textiles from ordinary fabrics like cotton, nylon, and polyester. To address this issue, different methods have been investigated which include functionalization of ordinary fabrics with conductive inks or pastes via screen printing, nanowire-coated threads, electroplating, and embroidering conductive materials into fabrics. However, earlier methods either require dedicated equipment or fabrication processes that are complex, expensive, and incompatible for large-scale production, lack uniformity or sacrifice from the natural comfort of the fabric. In order to use textiles as biopotential sensors, they need to be flexible, durable, comfortable, and, biocompatible and have suitable electrical characteristics for signal acquisition. Several advantages of graphene—a single layer of carbon atoms arranged in a hexagonal lattice, having excellent electrical conductivity and elasticity combined with high ultimate strength while being extremely lightweight, leads to the direct application of it in electronic textiles (e-textiles) or smart garments. Owing to these features, the merger of graphene on a variety of textiles was recently demonstrated based on a low-cost, gel-free, washable, and scalable approach and the feasibility of the developed graphene textile electrodes were experimentally verified and benchmarked successfully against Ag/AgCl in multiple testing scenarios.

According to the present disclosure, a human computer interaction system and medium therethrough with a wearable signal acquisition system and a processor configured to implement an algorithm for the processing of ocular biopotentials offer a robust alternative that is ultimately more comfortable compared to "wet" electrodes, comprising one signal channel with three electrodes and five comments enabling a 97% convergence to standard AgCl counterparts.

An electrooculogram based human computer interaction system is provided.

An aspect of the system provides an electrooculogram-based human computer interaction system with a wearable signal acquisition system.

Another aspect of the system may provide an electrooculogram-based human computer interaction system with a wearable signal acquisition system based on graphene textile dry electrodes.

A further aspect of the system may provide an electrooculogram based human computer interaction system utilizing graphene-clad headband as wearable signal acquisition system.

A still further aspect of the system may provide an electrooculogram based human computer interaction system with wearable signal acquisition system with advanced performance matching compared to conventional wet electrodes.

The disclosed system provides an electrooculogram based human computer interaction (HCI) or human machine interface (HMI) system that enables control through signals produced by eye movement in different applications. Amongst the strengths of the EOG-based human machine interface system disclosed hereby lies in its robustness, adaptability and lightweight character with respect to different settings, as well as wearability regarding its dry electrode, more specifically graphene-clad textile centered design and signal acquisition medium characteristics.

The human computer interaction/human machine interface provides improved performance in comment generation and EOG signal utility, with the novel effect of graphene-clad headband as signal acquisition means emanating from the highly optimized placement of electrodes as channels, and their succinctness in terms of quantity and positioning.

The disclosure therefore broadly relates to a system devised to enable communication and interaction between a human being and a machine/computer in a robust manner that is superior to conventional wet electrode based methods in the art.

According to the system, forehead locations suitable for recording ocular biopotentials are realized with a wearable graphene textile paradigm, attaching textile electrodes into an elastic headband with embedded electronics. The capability of the graphene textile integrated headband in EOG monitoring and automatic recognition of multiple eye movement patterns are further realized with utility of a detection algorithm and system-level integration. Wearable headband styled system in the present disclosure demonstrates improved performance and potential of graphene e-textiles towards the development of advanced human-computer interaction (HCI) interfaces, as well as addressing problems evident in the state of the art.

BRIEF DESCRIPTION OF THE FIGURES

Accompanying drawings are given solely for the purpose of exemplifying an HCI/HMI system with head-wearable signal acquisition system and a processor.

The drawings are not meant to delimit the scope of protection as identified in the claims nor should they be referred to alone in an effort to interpret the scope identified in said claims without recourse to the technical disclosure herein.

DETAILED DESCRIPTION

The system may include an electrooculogram based human computer interaction/human machine interface (HCI/HMI) system comprising one signal acquisition means such as a signal acquisition system for obtaining biopotentials from the human body, and a processing means such as a processor for the processing of said biopotentials acquired through said signal acquisition system for enabling and facilitating human machine interactions in various settings.

The proposed electrooculogram based HMI/HCI system is utilizable as wearable technology, with said signal acquisition system being, for example, a graphene-clad electrode-bearing headband worn on the head of a human person. The wearable signal acquisition system may include graphene clad electrodes configured to monitor ocular biopotentials and output biopotential signals of unique patterns based on detection of different eye movements.

The proposed electrooculogram based HMI/HCI system is based on signal generation for the purpose of controlling an object such as a machine or a computer or any extra-human medium with the help of eye movements captured and processed via said processor. An object is defined as any circuitry capable of receiving either by wireless protocols or wired connection, processing, and/or displaying electronic data or control signals emanating from the system.

The proposed electrooculogram based HMI/HCI system renders different eye movements electrooculographically capturable and processable for generation of various commands and actions intended for an extra-human medium such as a computer, by way of classification and recognition algorithms undertaken by said processor.

Figure 1:
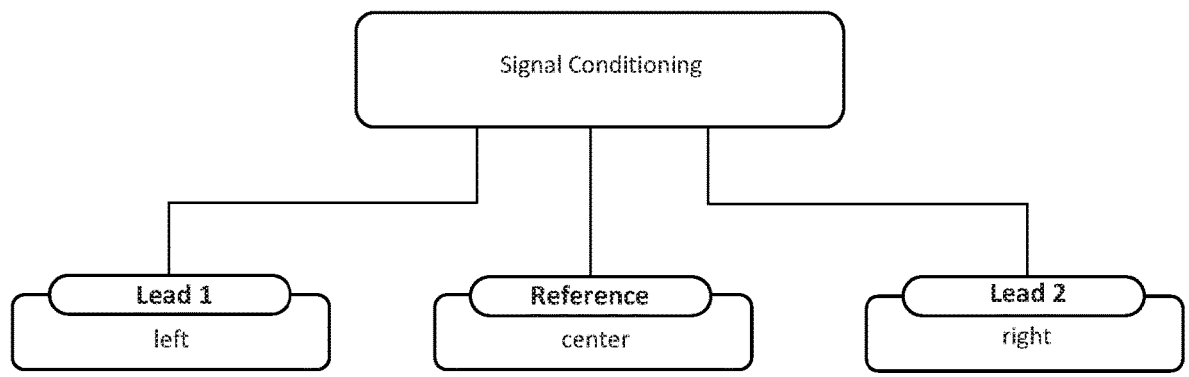
FIG. 1 demonstrates the readout circuitry, with electrode positions and a preprocessing step of signal conditioning according to one embodiment of the system.
Figure 2:
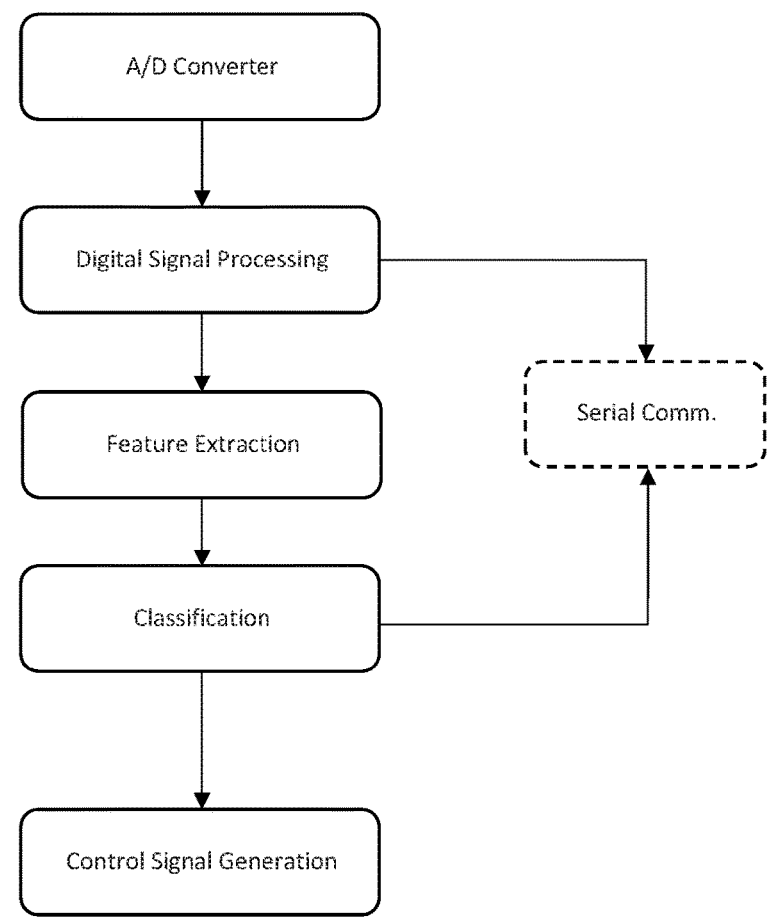
FIG. 2 demonstrates the flow diagram of the signal processing algorithm according to one embodiment of the system.

Referring to FIG. 1, the system-level block diagram of the proposed HCI interface is illustrated. In the front-end readout circuitry, heavily noise contaminated surface biopotentials are received using the fabricated graphene textile electrodes. As a next step, those surface biopotentials are fed into several filters and amplification stages. Specifications of the signal conditioning circuitry include very sharp roll-off band-pass filter in the frequency range of 0.3 to 10 Hz, adjustable gain from 600 to 4600 V/V, and variable offset of ±5 V.

Heavily noise contaminated biopotentials may be denoised in order to be rendered analytically usable. Once denoising is executed, biopotential signal is digitized using a built-in analog-to-digital converter (ADC) of an 8-bit microcontroller unit. In an embodiment, this analog-to-digital conversion step may be executed by a dedicated ADC unit. The sampling frequency of the analog-to-digital conversion process may be 100 Hz. Further normalization of the biopotential signal is achieved, according to one embodiment, by a digital rolling average filter application.

In an embodiment, further normalized biopotential signal is delivered through a feature detection where, distinctive attributes such as rise and fall times, amplitude, local minima and maxima are measured. These measured attributes are checked whether if they match hardcoded thresholds, i.e. patterns set beforehand. Failure of a match results in classification as a unique pattern. Subsequently, according to detected patterns in the biopotential signal, control signals are generated. Classification of detected biopotentials due to different eye movements are used as different command signals to remotely execute commands, communicate with objects, control and/or operate objects, including but not limited to movement of a mouse cursor, where the said object is defined as any that has a means of receiving either by wireless protocols or wired connection, processing and/or displaying electronic signals emanating from the system.

Control signals are, according to one embodiment, generated in a way to enable a wide array of control and command capabilities. One scenario may include controlling a simple keyboard administered by said commands emanating from control signals. Yet another scenario may include controlling an eye mouse. Other embodiments include controlling a wheelchair, mimicking remote control protocols, home appliances such as a television with the aid of such control signal-based commands.

In an embodiment, conductive textiles are synthesized based on a scalable three-step coating approach, namely the dip-dry-reduce coating. In various embodiments, said dip-dry-reduce coating enabled graphene clad wearables are produced using ordinary fabric material such as nylon, cotton and polyester.

An embodiment posits the process for preparing conductive textiles as follows: Preparation of graphene oxide (GO) suspension based on the modified Hummer's method, followed by dipping of plain textiles (nylon, cotton etc.) into graphene oxide solution, leaving the wetted textile to dry at moderate temperatures (~80 degrees Celsius) which allows layering of graphene oxide around individual textile fibers, chemically treating the GO-coated textile with reducing agents like hydrazine or hydrogen iodide, and rinsing in deionized water to form stable, conductive, graphene cladding on textiles.

According to one embodiment, dimensional optimization is conducted on the GO-coated textile compliant with the requirements to detect electrooculograms from different spots on the forehead of a human being. In an embodiment, dimensions of 3 cm by 3 cm are selected. Pieces cut in desired dimensions are mounted on a headband with flexible sticky foams and sandwiched between a metallic snap fastener to establish electrical connection with the front-end circuitry. In an embodiment, said foam acts as a padding to improve skin-to-electrode contact, while also providing sufficient pressure to maintain conformal interface with the skin for acquisition of biopotential signals.

Since the amplitude of an electrooculogram signal is sensitive to relatively small variations in positions of electrodes as documented in the art, depending on the applications and settings different numbers of electrodes as well as locations are a matter of consideration. Commonly in clinical monitoring, a signal acquisition unit with two channels, one for horizontal EOG (hEOG) and one for vertical EOG (vEOG) are used to record raw biopotential signals referred to as electrooculograms. This configuration dictates usage of five electrodes, where one electrode is placed at the outer canthus of the left and right eye for detecting lateral eye movements (EMs); whereas the remaining two are attached above and below one eye for collecting transverse eye activity, and last electrode being placed centrally on the forehead as reference. Most comfortable approach on the user end for wearable devices is to achieve electrooculogram detection only from locations selected on the forehead of a human being, such that the electrodes can easily be integrated onto an elastic headband or a similar garment. Most forehead EOG configurations employ two channels with four electrodes, where one is shared between channels and detects four different saccadic movement patterns (up, down, left, right EMs) to execute various commands. According to the system, a novel electrode positioning configuration to detect the same number of differing EM patterns (hence control commands) with only three electrodes (including the reference) and one channel is proposed. Accordingly, the electrode count is reduced while the number of unique signal patterns output by the system to implement different command actions are maximized. In an example embodiment, additional electrodes can be placed above and/or below eyes to detect vertical eye motions to further increase the number of unique signal patterns and thereby command actions that can be generated with eye movements.

According to one embodiment of the system, three electrodes are fixedly positioned on the forehead where two of the electrodes are placed decidedly and substantially above left and right eyes towards the temples, and a reference electrode is placed halfway between said two electrodes. Locations in this, as well as other embodiments of the system are optimally selected in performance basis for saccadic, blink and fixation EMs. More so, detected biopotentials are expected to be more appropriately identified with the thresholding algorithm as amplitudes and patterns of EM differ greatly among various positioning alternatives, among which the one stronger in terms of magnitude is considered ideal.

Figure 3:
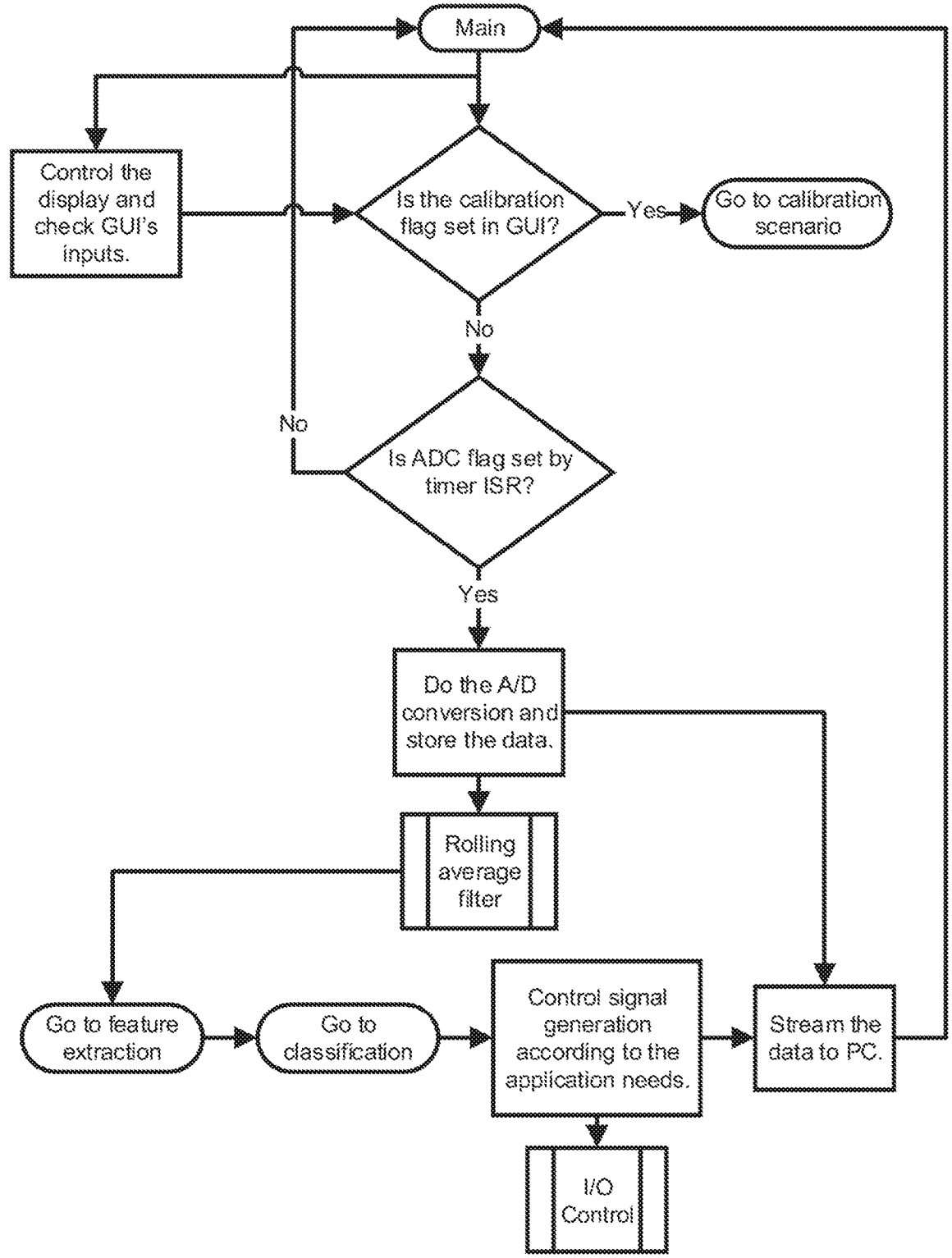
FIG. 3 demonstrates a summarized flowchart of the volunteer blinking and four saccadic eye movement detecting algorithm according to one embodiment.

As electrooculogram waveforms display exclusively patterned signals defined for each eye movement (EM), their differences in shape and magnitude as well as duration are considered. In an embodiment of the system, a unique signature for each EM pattern is hard-coded into the software, enabling the processor to perform automatic detection thereof. For this purpose, a sequential, multi-step, fixed thresholding algorithm is developed in at least one embodiment. Referring to the summarized flowchart in FIG. 3, the algorithm is responsible for implementation of tasks as follows: The algorithm first maintains synchronization with the GUI, following which it digitizes the denoised signal. Then, the algorithm normalizes the data, following which information and features are extracted from said normalized denoised signals. Extracted information and data features are then compared to hard-coded patterns. Next, signals are classified as a result of comparison and the algorithm proceeds to generate control signals pertaining to specific application requirements. In different embodiments, control signals generated as a result of the algorithm may be clock pulses or control comments.

In an embodiment of the system, taking into consideration the "soft" real-time character of possible tasks to be executed with control commands, a periodic approach scheduling is assumed with the internal timer of the processing unit, e.g. an MCU. In still another embodiment of the system, algorithm development is centered around emphasis of real-time operating system (RTOS) avoidance as well as complicated digital signal processing (DSP) techniques, making the feature extraction and/or classification algorithms used in the system as less demanding as possible and operable on slow processing speeds perhaps under 20 MHz. This enables the algorithms to be implemented on general-purpose, small size and low cost microcontroller units (MCUs).

According to one embodiment of the system, timer interrupt service routine (ISR) is programmed to perform several tasks which includes, triggering of an A/D conversion according to the desired sampling rate (e.g. 100 Hz), measuring the duration of potential EMs, running a time window and continuously checking and controlling the inputs and outputs (I/O).

Figure 4:
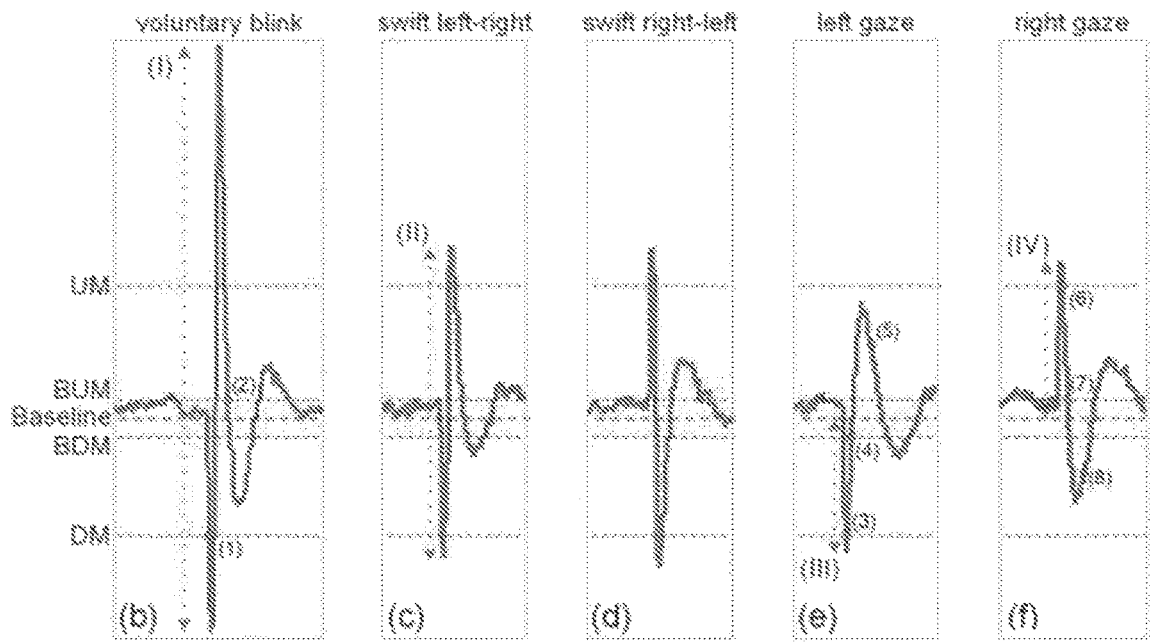
FIG. 4 demonstrates different types of detected eye movements and their five exclusive signal patterns as well as hard coded critical threshold levels according to one embodiment.
Figure 5:
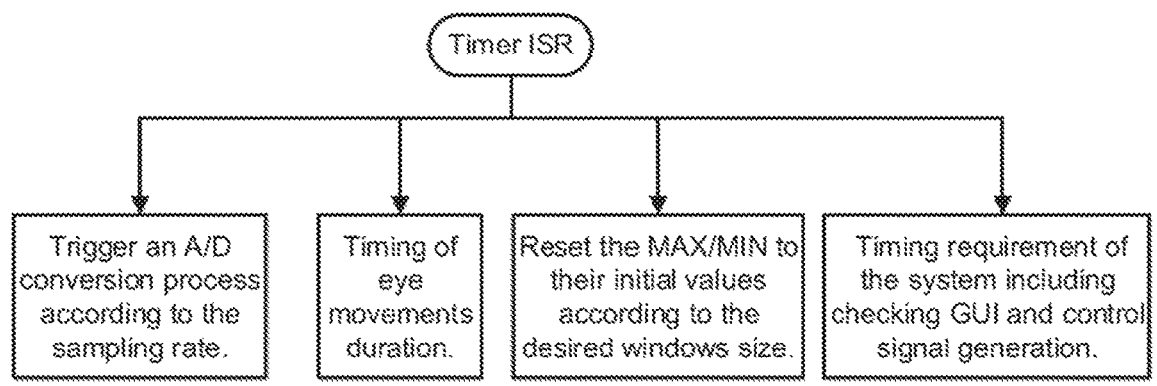
FIG. 5 demonstrates the timer interrupt service routine (ISR) working block diagram for the proposed embedded software according to one embodiment.

Referring to FIG. 4, to construct a pattern model, as a primary task is to regularly track the location of the real-time EOG signal which may include various EMs, five threshold levels were defined and named as "up margin" (UM), "baseline up-margin" (BUM), "baseline", "baseline down-margin" (BDM) and "down margin" (DM). These threshold lines along with the duration and peak-to-peak amplitude of defined EMs are measured and hardcoded to the system in advance. On literature, most of the calibration methods either adjust thresholds in software level and leave hardware level parameters untouched or, the operator adjusts signals in hardware level according to the software threshold needs and always leave software parameters constant. In the system, a mixture of both where the system is calibrated during training sessions with the addition of an offset to the signals by directing the participant to hold their gaze at the central point and fixate eyes at the primary position is adopted. The baseline value is configured to guarantee the signal to be in the positive domain below 5 V level; is fixed at 1.5 V. Once the desired offset is ensured, several EMs of each type are performed so that the gain level could be adjusted accordingly to prevent output saturation.

In an embodiment, at the software level, thresholds for UM and DM are configured based on several constraints. First, blinks, swift moves, and right gaze must pass through and intersect the UM but left gaze must not. Second, all moves must pass through and intersect DM but right gaze must not. In an embodiment, UM and DM are 2.1 V and 1 V, respectively. Third, BUM and BDM levels with respect to the baseline are selected according to baseline fluctuation; which is empirically determined to be ±0.1 V. In various embodiments, especially in long-term use, variation of signal amplitude due to environmental, physiological or physical factors such as feeling of tiredness or change in skin-electrode impedance could be critical and require recalibration of gain and offset parameters accordingly.

Figure 6:
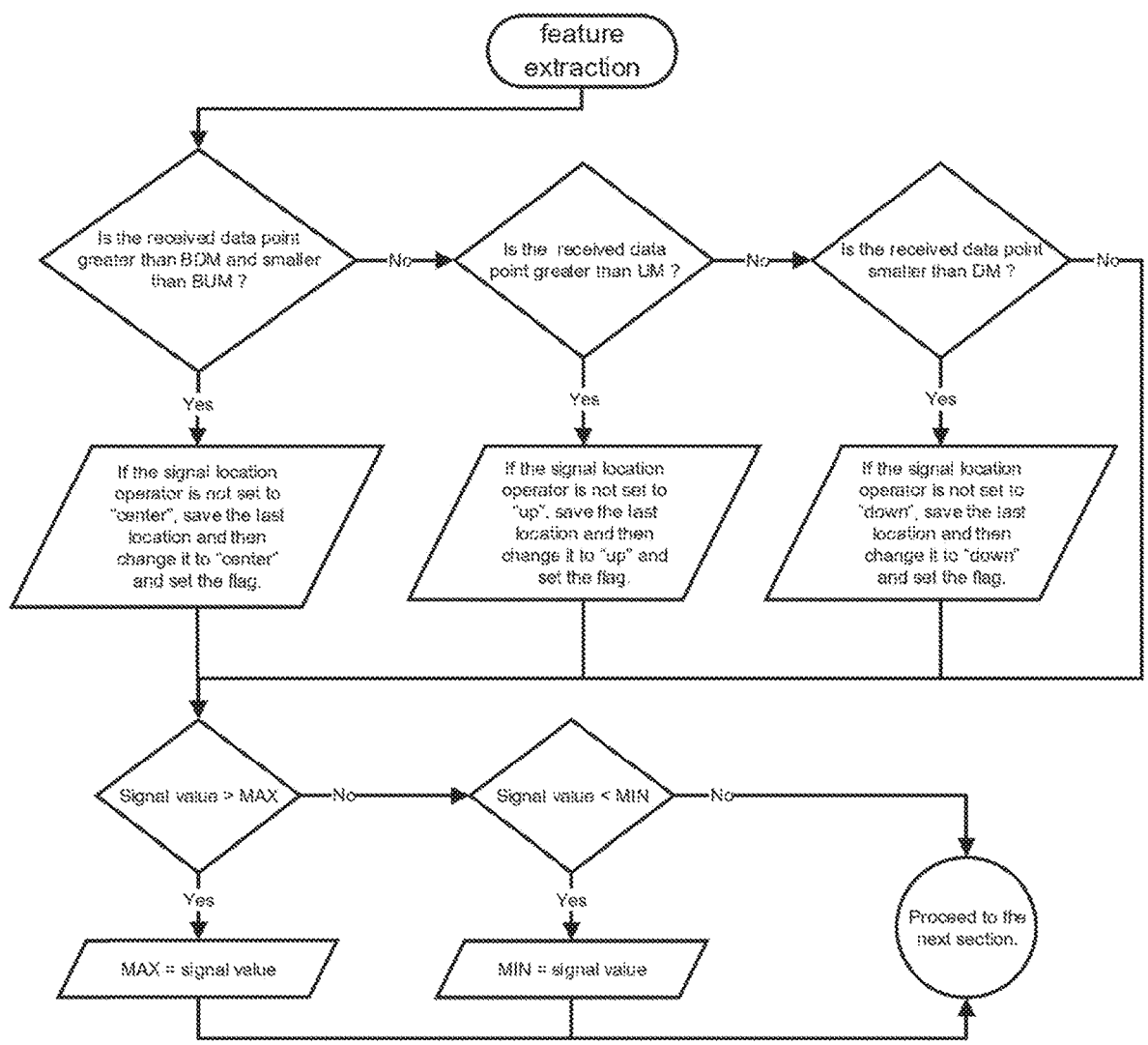
FIG. 6 demonstrates a detailed feature extraction section of the proposed automatic eye movement detection algorithm according to one embodiment.

In the feature extraction according to the system displayed in FIG. 6, after normalization of the signal using a rolling average filter, which is implemented for minimizing the effect from stabilization phenomena of fixation, if the signal appears to have a large value than UM, the location of said signal is labeled as "up", whereas if it lies in between BUM and BDM the location will be designated as "center" and, if the data value is less than DM, the location of the signal is labeled as "down". The location operator is left unchanged if the signal is in between UM and BUM, or DM and BDM, to avoid oscillation of location operator in critical cases near margins. If the location operator changes, a flag will be set to alert the algorithm to implement the necessary actions in the classification section.

In an embodiment of the system, as the algorithm detects the defined EMs, it also avoids detection of undefined EMs and responding as one of the defined patterns. For instance, spontaneous or reflex blinks (which can have several shapes, durations, or amplitudes depending on the context), or small degree saccadic eye movements (mainly resembling left/right moves but with a smaller magnitude may occur during sedentary activities like reading or writing) and must be excluded from detection. Additionally, the main parameter which distinguishes the swift left-right move and different types of blinks from each other is differences in their amplitude. Therefore, measurement of the signal amplitude is critical for reliably constructing the pattern model.

Figure 7:
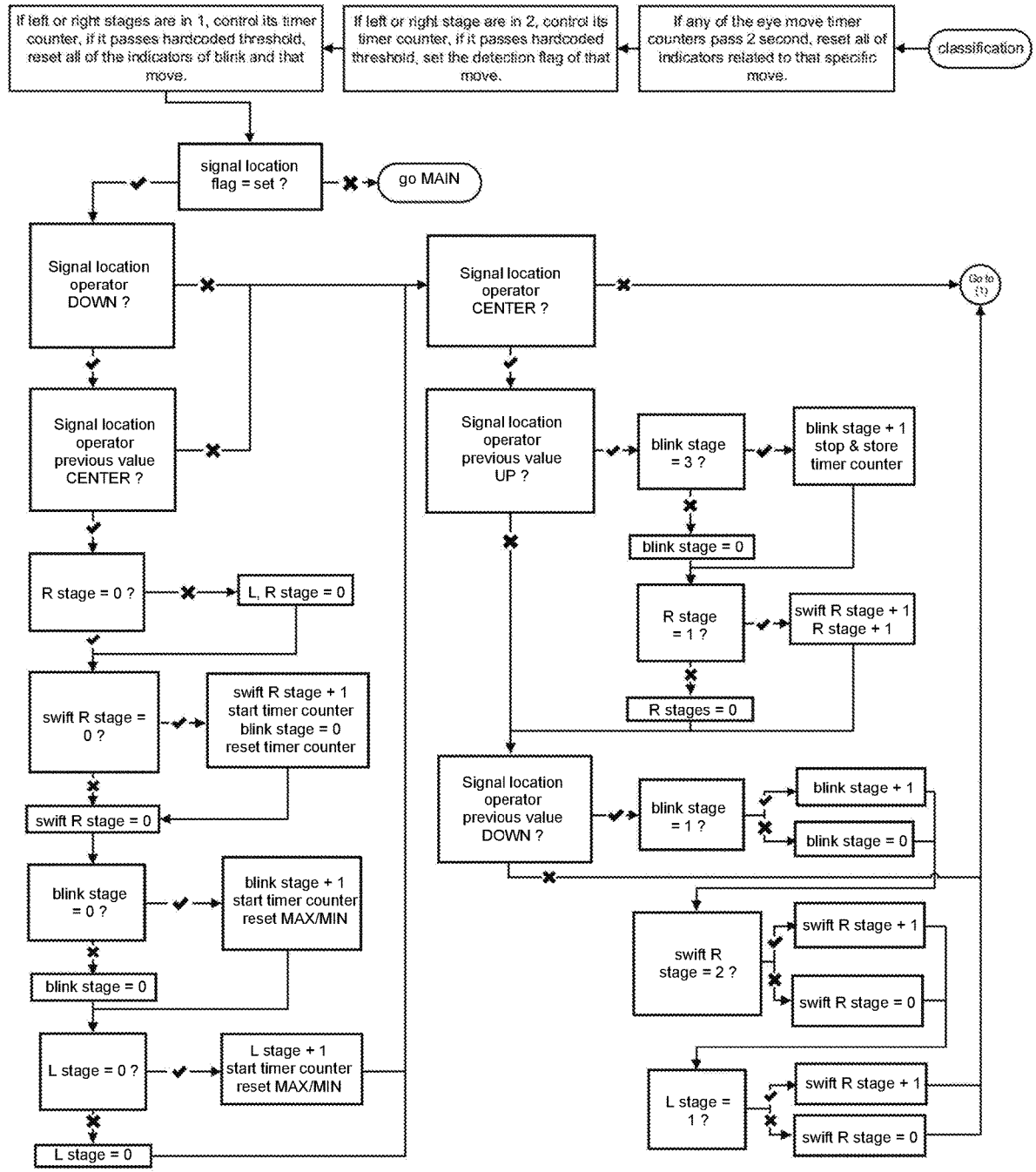
FIG. 7 demonstrates a first part of the detailed classification section for the proposed automatic eye movement detection algorithm according to one embodiment.
Figure 8:
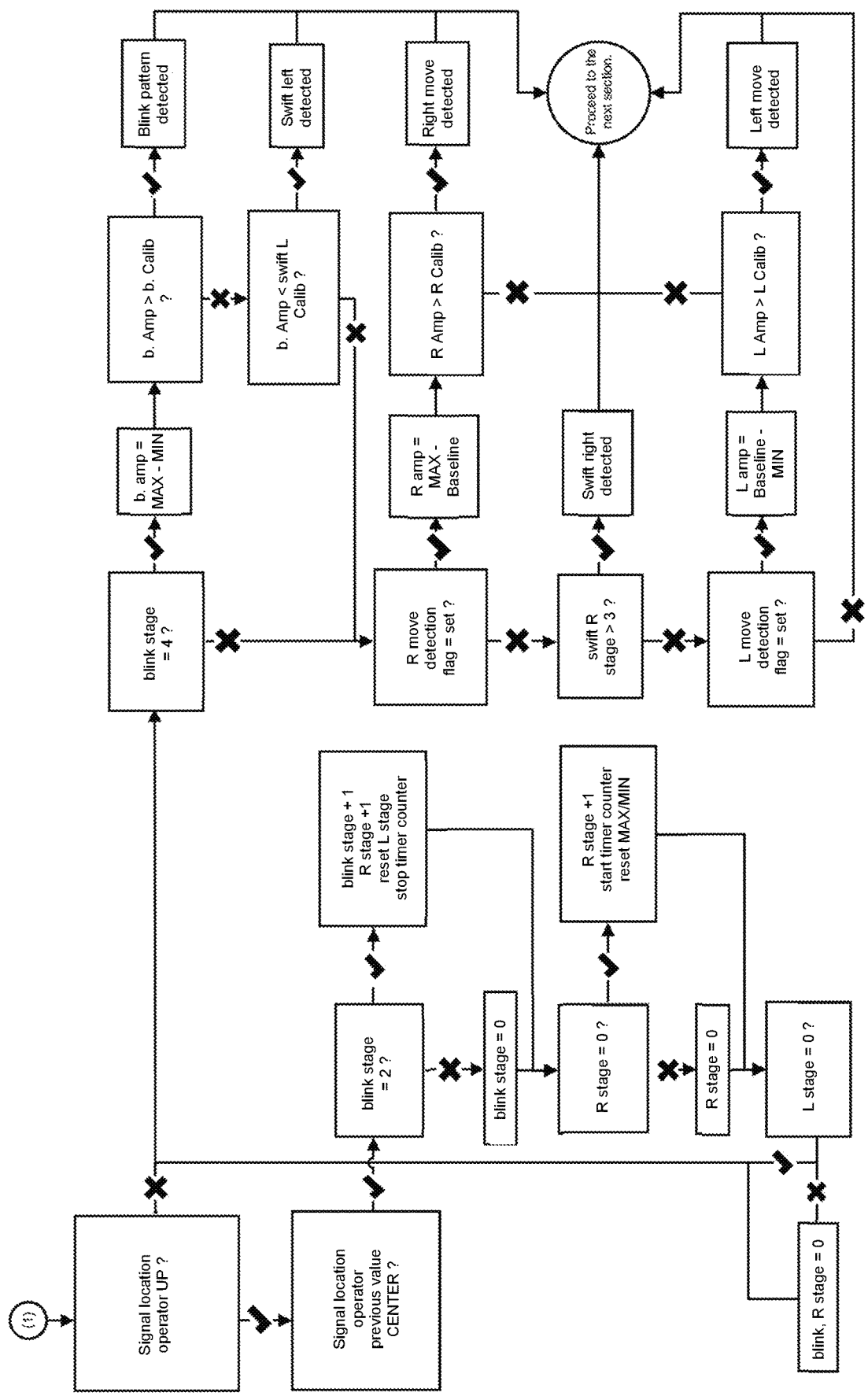
FIG. 8 demonstrates a second part of the detailed classification section for the proposed automatic eye movement detection algorithm according to one embodiment.

In case of a flag alert for a signal location change, the system enters the classification section (FIGS. 7 and 8); where the algorithm tracks the signal that occurred to identify its pattern. The volunteer blink complex (first signal in FIG. 4) first changes its location from center to down, then returns to the center, then rises to up (stage 3), and eventually returns to primary central position (stage 4) with the following of an undershoot. As soon as the signal enters stage 1 (marked as (1) in FIG. 4), a counter starts keeping the time and stops when the signal reaches stage 4 (marked as (2) in FIG. 4). The interval between time 1 and 2 is measured as the signal duration and it must be lower than a set threshold.

Swift left-right gaze (second signal of FIG. 4) and the volunteer blink patterns are nearly identical in terms of the locations at when a change in signal pattern occurs. Therefore, the stage indicator for a swift left-right gaze moves like the stage variable of a volunteer blink, but with a significantly different amplitude. Its amplitude (noted as "II" in FIG. 4) must be lower than its threshold and definitely, it is smaller than the threshold introduced for the blink amplitude (noted as "I" in FIG. 4). Swift right-left gaze (third signal in FIG. 4) signal changes its pattern opposite to the behavior of a blink, where it first starts by rising to up position (stage 1), then returns to center (stage 2), then falls down (stage 3), and finally returns to center (stage 4) with the following of an overshoot. Since the unique pattern of swift right-left gaze differs it from all other movements, no other threshold is required for building its model.

Left gaze (fourth signal in FIG. 4) first changes its location from center to down (stage 1) and then returns to center (stage 2) with following of an overshoot which never reaches the UM level. The algorithm for detecting left gaze relies on two timer counters, one counts the duration between "3" and "4" which should not pass a specific threshold, and the other is a countdown timer which gives the system a short duration to check and find if the signal goes to "up" location or not. The same detection system stands for the right gaze (fifth signal in FIG. 4), which is essentially the reverse pattern of a left gaze. In the right gaze signal first rises up (stage 1) and then returns to center with following of an undershoot which must not intersect DM. Its timer counters control the duration threshold between its stages 1 and 2, and its down counter provides an interval to check if the signal passes UM or not before detecting the pattern as a valid EM.

Then, the algorithm computes the amplitude of the signal and compares it with its respective threshold value. In one embodiment of the system, for calculating the amplitude of the pattern, ultimate high hillock and ultimate low valley points are found out by continuously comparing the maximum and minimum data values with each other in a predefined time window. If the system detects specific attribute of the EOG signal as one of the five defined EMs, it will initiate a unit pulse with different amplitude for each detected pattern. Additionally, GUI displays the detected EM's name, amplitude, and duration. Moreover, a buzz sound is generated by the computer to alert the operator of an EM detection event.

Human machine interface system of the disclosure is distinctively superior when compared against conventional AgCl i.e. "wet" electrodes in dryness as well as dry electrode methods in its novel and high-performance enabling positioning over the course of a human head-wearable configuration. In various embodiments, a wearable technology paradigm is utilized to detect biopotentials from the human forehead in electrooculography, processed with the aid of a processing means with an algorithm classifying and recognizing, as well as producing commands according to various embodiments. In entirety, said EOG-based HMI/HCI system offers a comfortable, smart, long-term utilizable control environment with novel electrode placement schema and graphene-clad textile utility.

The methods, devices, processing, circuitry, and logic described above may be implemented in many different ways and in many different combinations of hardware and software. For example, all or parts of the implementations may be circuitry that includes an instruction processor, such as a Central Processing Unit (CPU), microcontroller, or a microprocessor; or as an Application Specific Integrated Circuit (ASIC), Programmable Logic Device (PLD), or Field Programmable Gate Array (FPGA); or circuitry that includes discrete logic or other circuit components, including analog circuit components, digital circuit components or both; or any combination thereof. The circuitry may include discrete interconnected hardware components or may be combined on a single integrated circuit die, distributed among multiple integrated circuit dies, or implemented in a Multiple Chip Module (MCM) of multiple integrated circuit dies in a common package, as examples.

Accordingly, the processor circuitry may store or access instructions for execution, or may implement its functionality in hardware alone. The instructions may be stored in memory, which is a tangible storage medium that is other than a transitory signal, such as a flash memory, a Random Access Memory (RAM), a Read Only Memory (ROM), an Erasable Programmable Read Only Memory (EPROM); or on a magnetic or optical disc, such as a Compact Disc Read Only Memory (CDROM), Hard Disk Drive (HDD), or other magnetic or optical disk; or in or on another machine-readable medium. A product, such as a computer program product, may include a storage medium and instructions stored in or on the medium, and the instructions when executed by the circuitry in a device may cause the device to implement any of the processing described above or illustrated in the drawings.

The implementations may be distributed. For instance, the circuitry may include multiple distinct system components, such as multiple processors and memories, and may span multiple distributed processing systems. Parameters, databases, and other data structures may be separately stored and managed, may be incorporated into a single memory or database, may be logically and physically organized in many different ways, and may be implemented in many different ways. Example implementations include linked lists, program variables, hash tables, arrays, records (e.g., database records), objects, and implicit storage mechanisms. Instructions may form parts (e.g., subroutines or other code sections) of a single program, may form multiple separate programs, may be distributed across multiple memories and processors, and may be implemented in many different ways. Example implementations include stand-alone programs, and as part of a library, such as a shared library like a Dynamic Link Library (DLL). The library, for example, may contain shared data and one or more shared programs that include instructions that perform any of the processing described above or illustrated in the drawings, when executed by the processor circuitry.

In some examples, each unit, subunit, and/or module of the system may include a logical component. Each logical component may be hardware or a combination of hardware and software. For example, each logical component may include an application specific integrated circuit (ASIC), a Field Programmable Gate Array (FPGA), a digital logic circuit, an analog circuit, a combination of discrete circuits, gates, or any other type of hardware or combination thereof. Alternatively or in addition, each logical component may include memory hardware, such as a portion of the memory, for example, that comprises instructions executable with the processor or other processors to implement one or more of the features of the logical components. When any one of the logical components includes the portion of the memory that comprises instructions executable with the processor, the logical component may or may not include the processor. In some examples, each logical components may just be the portion of the memory or other physical memory that comprises instructions executable with the processor or other processor to implement the features of the corresponding logical component without the logical component including any other hardware. Because each logical component includes at least some hardware even when the included hardware comprises software, each logical component may be interchangeably referred to as a hardware logical component.

Various implementations have been specifically described. However, many other implementations are also possible.

The invention claimed is:

1. An electrooculogram based interaction system comprising:
   a wearable signal acquisition system wearable on a human head; and
   a processor;
   wherein said wearable signal acquisition system further comprises three graphene clad electrodes, one of which is a reference electrode and the remaining two electrodes are configured one per each eye, configured to detect ocular biopotentials due to different eye movements and output biopotential signals of unique patterns;
   said three electrodes are colinearly positioned on said wearable signal acquisition system such that electrode count is reduced and ocular biopotentials representing different saccadic movement patterns comprising up, down, left and right eye movement are detected as the biopotential signals; and
   said processor is configured to implement a signal processing-based algorithm stored in memory for detection and classification of said biopotential signals according to predefined patterns.

2. An electrooculogram based interaction system as set forth in claim 1 wherein the controller is configured to use said classification of detected ocular biopotentials due to different eye movements to generate different command signals, said command signals used to remotely execute commands on objects, communicate with objects, control objects and/or operate objects, wherein said objects comprise circuitry to receive and process said different command signals.

3. An electrooculogram based interaction system as set forth in claim 2, wherein said controller is configured to transmit said command signals by wireless protocols or wired connection, to initiate processing and/or display by said object.

4. An electrooculogram based interaction system as set forth in claim 2, wherein said command signals comprise instructions for movement of a mouse cursor of said object.

5. An electrooculogram based interaction system as set forth in claim 1, wherein said controller is configured to generate a plurality of different command actions corresponding to detection and classification of said biopotential signals according to different predefined patterns results.

6. An electrooculogram based interaction system as set forth in claim 1 further comprising additional electrodes, wherein said additional electrodes are configured for placement above and/or below eyes to detect vertical eye motions to increase a number of the unique patterns and the controller is configured to generate an increased number of command actions corresponding to the increased number of unique patterns.

7. An electrooculogram based interaction system as set forth in claim 1 wherein said three electrodes are in connection with a signal conditioning module for denoising received signals.

8. An electrooculogram based interaction system as set forth in claim 1 wherein said wearable signal acquisition system is a graphene-clad headband.

9. An electrooculogram based interaction system as set forth in claim 1 wherein said processor is configured to implement a multi-step thresholding algorithm whereby fixations, different saccadic eye movements, volunteer and involuntary eye blinks are detected and distinguished.

10. An electrooculogram based interaction system as set forth in claim 9 wherein said multi-step thresholding algorithm is configured to detect four different horizontal saccadic eye movements, volunteer eye blinks, involuntary eye blinks, fixations, vertical eye movements or any combination thereof.

11. An electrooculogram based interaction system as set forth in claim 1 wherein said system further comprises a graphical user interface.

12. An electrooculogram based interaction system as set forth in claim 1, wherein said system further comprises a connectivity circuitry for establishing data transmission for display.

13. A method comprising:
   processing and classifying, with a controller, raw biopotentials originating from eye movements for controlling a human machine interface comprising a GUI by:
   GUI synchronization;
   digitization, where a biopotential acquired by a signal acquisition system is converted from analog to digital;
   normalization, where digitized signals are normalized using at least one instance of a rolling average filter;
   feature extraction, where normalized signals are categorized according to locations next to hard-coded margins;
   classification, where categorized signals are classified based on computed amplitude comparison against threshold values; and
   control signal generation; where depending on a desired outcome of a given setting, control signals are produced to achieve specific tasks.

14. The method of claim 13, further comprising a preprocessing step for denoising acquired biopotentials.

15. The method of claim 13, wherein the signal acquisition system comprises a graphene-clad headband in signal communication with the controller.

* * * * *